United States Patent [19]

Dubroeucq et al.

[11] Patent Number: 4,808,599
[45] Date of Patent: Feb. 28, 1989

[54] BENZO[b]THIOPHENE- AND BENZO[b]FURANCARBOXAMIDE DERIVATIVES, PHARMACEUTICAL COMPOSITIONS AND USE

[75] Inventors: Marie-Christine Dubroeucq, Enghien-les-Bains; Christian Renault, Taverny, both of France

[73] Assignee: Rhone-Poulenc Sante, Courbevoie, France

[21] Appl. No.: 58,780

[22] Filed: Jun. 5, 1987

[30] Foreign Application Priority Data

Jun. 5, 1986 [FR] France ............... 86 08110

[51] Int. Cl.$^4$ ............... A61K 31/38; A61K 31/445; C07D 333/68; C07D 409/02
[52] U.S. Cl. ............... 514/320; 514/324; 514/443; 514/469; 546/196; 546/202; 549/57; 549/60; 549/467
[58] Field of Search ............... 546/196, 202; 549/57, 549/60, 467, 468, 469; 514/320, 324, 443, 444, 469

[56] References Cited

PUBLICATIONS

Zavala et al, *European Journal of Pharmacology*, vol. 106 (1984), pp. 561–566.
Mestre et al, *European Journal of Pharmacology*, vol. 112 (1985), pp. 257–260.
Mizoule et al, *Life Sciences*, vol. 36 (1985), pp. 1059–1068.
Hashem et al, CA, vol. 99, 1983, 99:211859u, p. 586.
Hishmat et al, CA, vol. 100, 1984, 100:22531j, p. 482.
Morrison et al, Textbook "Organic Chemistry", 1973, Allyn and Bacon, Inc., Boston, MA, p. 746.

*Primary Examiner*—Robert W. Ramsuer
*Attorney, Agent, or Firm*—Stevens, Davis, Miller & Mosher

[57] ABSTRACT

Compounds of formula:

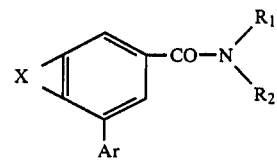

in which $R_1$ and $R_2$ are each alkyl, cycloalkyl or phenyl, or $NR_1R_2$=piperidine, Ar is optionally substituted phenyl or thienyl, and X< is one of the following linkages:

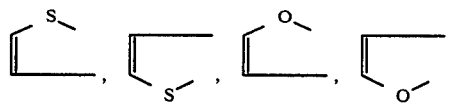

are useful as anxiolytic, antianginal and immunomodulatory agents. They may be made by reaction of an amine with the corresponding acid chloride.

11 Claims, No Drawings

BENZO[B]THIOPHENE- AND BENZO[B]FURANCARBOXAMIDE DERIVATIVES, PHARMACEUTICAL COMPOSITIONS AND USE

The present invention relates to benzo[b]thiophene and benzo[b]furancarboxamides, their preparation and pharmaceutical compositions containing them.

The compounds of the invention may be represented by the formula:

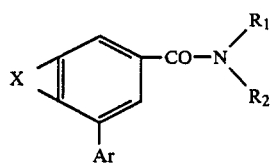
(I)

in which $R_1$ and $R_2$, which may be identical or different, each represent a straight- or branched-chain alkyl group of 1 to 4 carbon atoms, a cycloalkylalkyl group having 1 to 3 carbon atoms in the alkyl and 3 to 6 carbon atoms in the cycloalkyl or a phenyl group, and $R_1$ and $R_2$, together with the nitrogen atom to which they are attached, may also form a piperidine ring, Ar represents phenyl, thienyl, or phenyl substituted by one or two substituents selected from the group consisting of halogen (e.g. fluorine, chlorine or bromine), alkyl of 1 to 4 carbon atoms, alkoxy of 1 to 4 carbon atoms, nitro and trifluoromethyl, and $X<$ represents one of the following linkages:

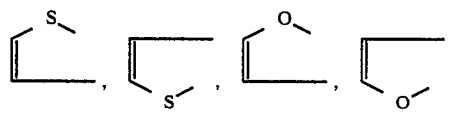

In other words, the compounds of formula (I) of the present invention are of one of the following 4 formulae:

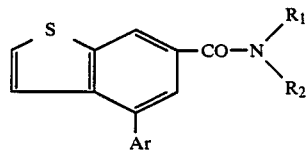
(II)

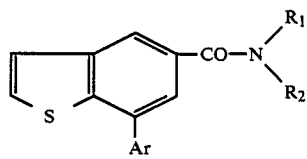
(III)

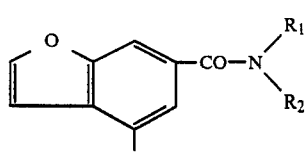
(IV)

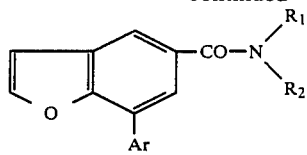
(V)

in formulae (II), (III), (IV) and (V), Ar, $R_1$ and $R_2$ have the same meanings as in formula (I).

When the group $NR_1R_2$ contains one or more asymmetric carbon atoms, for a given meaning for Ar, $R_1$ and $R_2$, there are several stereoisomers corresponding to the plane formula (I). These various stereoisomers and the corresponding racemic forms form part of the invention.

Compounds of formula (I) may be prepared by reacting an amine of formula:

(VI)

or a salt of this amine with a compound of formula:

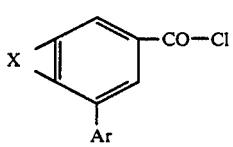
(VII)

in which Ar, $X<$, $R_1$ and $R_2$ have the same meanings as in formula (I). Suitable salts of the amine of formula (VI) include the hydrochloride and the p-toluenesulfonate.

This reaction may be carried out using methods known per se, which enable an acid chloride to be converted into carboxamide, such as those described by C. A. BUEHLER and D. E. PEARSON, Survey of Organic Synthesis, Wiley Interscience, 1970, p. 804.

It is particularly advantageous to react the acid chloride of formula (VII) with the amine of formula (VI) in the presence of a tertiary amine such as triethylamine, in an inert solvent such as toluene, chloroform or methylene chloride, at a temperature between 20° C. and the boiling point of the solvent. In the case where a salt of the amine of formula (VI) is used, at least two equivalents of the tertiary amine should be used for each equivalent of the amine salt.

The acid chlorides of formula (VII) may be obtained by the action of a chlorinating agent such as thionyl chloride on an acid of formula:

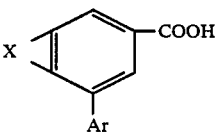
(VIII)

in which Ar and $X<$ have the same meanings as in formula (I).

This reaction may be carried out in the absence of a solvent or in an inert solvent such as chloroform or toluene, preferably at the boiling point of the mixture.

Some acids of formula (VIII) are known. These are 4-(4-methylphenyl, 4-methoxyphenyl and 4-chlorophenyl)-6-benzo[b]furancarboxylic acids (A. J. HASHEM, Journal F. Prakt. Chemie, 319(4), 689–692 (1977)).

Other acids of formula (VIII) may be prepared by adapting the method described by L. S. EL ASSAL and A. H. SHEHAB, J. Chem. Soc. 1658–1662, 1961 which consists in heating, to a temperature of between 100° and 120° C., a compound of formula:

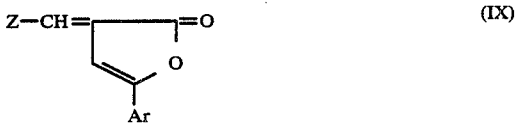

in which Z is a 2-thienyl, 3-thienyl, 2-furyl or 3-furyl radical and Ar has the same meaning as in formula (I), in a 50:50 mixture of methanesulfonic acid and acetic acid.

The compounds of formula (IX) may be obtained by reacting 2- or 3-thiophenecarboxaldehye or 2- or 3-furancarboxaldehyde with a derivative of formula:

in which Ar has the same meaning as in formula (I), in the presence of acetic anhydride and an alkali metal acetate such as sodium or potassium acetate, at a temperature of 80° to 90° C.

Compounds of formula (I) in which $R_1$ is alkyl of 1 to 4 carbon atoms and $R_2$, Ar and $X<$ have the same meanings as before, may be prepared by alkylating compounds of formula:

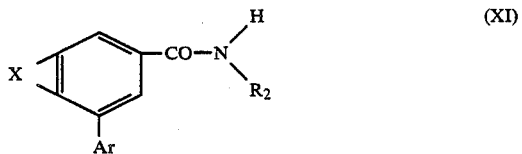

in which $R_2$, Ar and $X<$ have the same meanings as in formula (I), with an alkyl halide of formula:

in which Hal is a halogen atom and $R'_1$ is alkyl of 1 to 4 carbon atoms. This reaction may be carried out according to a method known per se, such as that described by A. W. JOHNSTONE and M. E. ROSE, Tetrahedron 25, 2169–73, 1979. An advantageous process consists in operating in a nitrogen atmosphere, at ambient temperature, in the presence of a strong base such as potassium hydroxide in powder form in a solvent such as dimethyl sulfoxide.

Compounds of formula (XI) may be prepared by reacting an amine of formula:

in which $R_2$ has the same meanings as in formula (I), with a compound of formula (VII) in which Ar and $X<$ have the same meanings as in formula (I). This reaction may be carried out under the same conditions as those mentioned above for preparing compounds of formula (I) from compounds of formula (VII) and amines of formula (VI).

The stereoisomers of compounds of formula (I) in which the group $NR_1R_2$ contains one or more asymmetric carbon atoms may be obtained by resolving the racemic forms, for example, by chiral column chromatography according to W. H. PIRKLE et al., Asymmetric Synthesis, vol 1, Academic Press (1983) or by synthesis from chiral precursors.

The reaction mixtures obtained by the various processes described above are treated according to conventional physical methods (evaporation, extraction, distillation, crystallization and chromatography) or chemical methods (preparing the salt and recovering the base or the acid) in order to isolate the compounds of formula (I) in the pure state.

The compounds of formula (I) have useful pharmacological properties. They bind themselves to peripheral type benzodiazepine receptors and are useful as anxiolytic, antianginal and immunomodulatory agents.

The affinity of the compounds of formula (I) for peripheral type benzodiazepine receptor sites was determined using the protocol of BRAESTRUP et al., Proc. Natl. Acad. Sci. USA, 74, 3805 (1977) on rat kidney membranes using $^3$H-PK 11195 (i.e. N-methyl-N-(1-methylpropyl)-1-(2-chlorophenyl)isoquinoline-3-carboxamide) as the ligand. This affinity corresponds to an inhibition constant (Ki) of between 0.001 and 0.200 μM.

The compounds of the invention have a low toxicity. Their $LD_{50}$ by the oral route in the mouse is greater than 200 mg/kg. The $LD_{50}$ were calculated after 3 days of observation using the cumulative method of J. J. REED and H. MUENCH, Amer. J. Hyg., 27, 493 (1938).

The compounds of formula (I) in which $R_1$ and $R_2$, which may be identical or different, are straight- or branched-chain alkyl of 1 to 4 carbon atoms and Ar is phenyl, phenyl substituted by halogen or nitro, or 2-thienyl, are particularly useful.

The following compounds are especially useful: N-methyl-N-(1-methylpropyl)-4-phenylbenzo[b]furan-6-carboxamide;
N-methyl-N-(1-methylpropyl)-7-(2-chlorophenyl)benzo[b]thiophene-5-carboxamide;
N-methyl-N-(1-methylpropyl)-4-phenylbenzo[b]thiophene-6-carboxamide;
N-methyl-N-(1-methylpropyl)-7-(2-fluorophenyl)benzo[b]thiophene-5-carboxamide;
N,N-diethyl-7-(3-nitrophenyl)-benzo[b]thiophene-5-carboxamide;
N-methyl-N-(1-methylpropyl)-7-(2-thienyl)benzo[b]furan-5-carboxamide; and
N-methyl-N-(1-methylpropyl)-7-phenylbenzo[b]thiophene-5-carboxamide.

The following Examples illustrate the invention.

EXAMPLE 1

7-Phenylbenzo[b]thiophene-5-carboxylic acid (3 g) and thionyl chloride (2.6 cc) are heated for 2 hours at 90° C. in toluene (30 cc). The solvent and the excess thionyl chloride are evaporated under reduced pressure and toluene (30 cc) and triethylamine (5.1 cc) are added to the residue.

The mixture is stirred and diethylamine (1.23 cc) is added dropwise. The stirring is continued for 1 hour at ambient temperature (approx. 20° C.). The toluene is evaporated under reduced pressure and the residue is taken up with methylene chloride and an aqueous potassium carbonate solution. The mixture is stirred for 5 minutes, and the organic phase is separated, washed with water, dried over magnesium sulfate, and evaporated under reduced pressure. The residue obtained is chromatographed on silica gel using a cyclohexane:ethanol:ethyl acetate (80:10:10 by volume) mixture as the eluent.

After recrystallizing the residue in isopropyl ether, N,N-diethyl-7-phenylbenzo[b]thiophene-5-carboxamide (2 g), m.p. 78° C., is obtained.

The 7-phenylbenzo[b]thiophene-5-carboxylic acid may be prepared as follows:

5-Phenyl-3-(3-thienylmethylene)-2-furanone (44.7 g), methanesulfonic acid (220 cc) and glacial acetic acid (220 cc) are heated for 1 hour at 120° C. The mixture is cooled to 40° C., poured onto crushed ice and extracted with methylene chloride. The organic phase is washed with water and extracted with normal sodium hydroxide solution. The basic aqueous phase is washed with methylene chloride, acidified to pH 1 by adding an aqueous hydrochloric acid solution, and extracted with methylene chloride. The precipitate formed is filtered off and the organic phase is dried over magnesium sulfate and evaporated under reduced pressure. The evaporation residue and the precipitate are combined and stirred in ethyl acetate in the presence of silica gel (100 g). The silica is removed by filtration and the ethyl acetate evaporated under reduced pressure. This operation is repeated to produce 7-phenylbenzo[b]thiophene-5-carboxylic acid (29 g), m.p. 234° C.

The 5-phenyl-3-(3-thienylmethylene)-2-furanone may be prepared as follows:

Thiophene-3-carboxaldehyde (27 g), 3-benzoylpropionic acid (35.8 g), acetic anhydride (57 cc) and fused potassium acetate (16.5 g) are heated overnight at 80° C. The mixture is cooled to 40° C., chloroform is added, and the mixture is then poured onto crushed ice. The aqueous phase is extracted with chloroform, and the organic phase is dried over magnesium sulfate and evaporated under reduced pressure. The residue is stirred for 45 minutes in 40°-60° petroleum spirit. After filtering and drying the residue, 5-phenyl-3-(3-thienylmethylene)-2-furanone (49 g), m.p. 153° C., is obtained.

EXAMPLE 2

Potassium hydroxide powder (1.8 g) followed by N-(1-methylpropyl)-7-phenylbenzo[b]thiophene-5-carboxamide (2 g) and finally methyl iodide (0.8 cc) are added to dimethyl sulfoxide (12 cc) under a nitrogen atmosphere, with stirring. The reaction mixture is stirred for 1 hour 30 minutes at ambient temperature (approximately 20° C.) and poured into water (50 cc) and ethyl acetate (60 cc). The mixture is stirred for 15 minutes. The organic phase is decanted, washed with water, dried over magnesium sulfate and evaporated to dryness under reduced pressure. The residue is chromatographed on silica gel using a cyclohexane:ethyl acetate (50:50 by volume) mixture as the eluent. The fractions containing the product are combined, evaporated under reduced presure, and taken up with a mixture of water and ethyl ether. The organic phase is decanted, washed with water, dried over magnesium sulfate and evaporated under reduced pressure. The residue is stirred for 1 hour 30 minutes with 40°-60° petroleum spirit (20 cc), filtered and dried.

N-Methyl-N-(1-methylpropyl)-7-phenylbenzo[b]thiophene-5-carboxamide (1.2 g), m.p. 105° C., is thereby isolated.

The N-(1-methylpropyl)-7-phenylbenzo[b]thiophene-5-carboxamide may be prepared as follows:

the reaction is carried out as in Example 1, starting with 7-phenylbenzo[b]thiophene-5-carboxylic acid (3 g) in toluene (30 cc) and thionyl chloride (2.6 cc) and then adding triethylamine (9.94 cc) and 2-butanamine (1.2 cc) in toluene (30 cc). After chromatography of the residue on silica gel using a cyclohexane:ethyl acetate (50:50 by volume) mixture as the eluent, N-(1-methylpropyl)-7-phenylbenzo[b]thiophene-5-carboxamide (2.35 g), m.p. 195° C., is obtained.

EXAMPLE 3

The reaction is carried out as in Example 1, starting with 4-phenylbenzo[b]thiophene-6-carboxylic acid (4 g) and thionyl chloride (3.5 cc) in toluene (40 cc) and then adding triethylamine (13.25 cc) and diethylamine (1.6 cc) in toluene (40 cc). After chromatography of the residue on silica gel using a cyclohexane:ethyl acetate (50:50 by volume) mixture as the eluent and then stirring the product collected in 40°-60° petroleum spirit (30 cc) and filtering, N,N-diethyl-4-phenylbenzo[b]thiophene-6-carboxamide (2.55 g), m.p 60° C. is isolated.

The 4-phenylbenzo[b]thiophene-6-carboxylic acid may be prepared as follows:

5-Phenyl-3-(2-thienylmethylene)-2-furanone (34.9 g), methanesulfonic acid (170 cc) and glacial acetic acid (170 cc) are heated for one hour at 120° C. The mixture is cooled to 40° C., poured onto crushed ice and extracted with methylene chloride. The organic phase is washed with water and extracted with a normal sodium hydroxide solution. The basic aqueous phase is washed with methylene chloride, acidified to pH 1 by adding an aqueous hydrochloric acid solution and extracted with methylene chloride. The precipitate formed is filtered, the organic phase is dried over magnesium sulfate and evaporated under reduced pressure. The evaporation residue and the precipitate are combined and chromatographed on silica gel using ethyl acetate as the eluent. 4-Phenylbenzo[b]thiophene-6-carboxylic acid (17.4 g), m.p. 222° C., is thereby isolated.

The 5-phenyl-3-(2-thienylmethylene)-2-furanone may be prepared as follows:

Thiophene-2-carboxaldehyde (27.4 cc), 3-benzoylpropionic acid (44.5 g), acetic anhydride (71 cc) and fused potassium acetate (20.5 g) are heated overnight at 80° C. The mixture is cooled to 40° C., chloroform is added and then poured onto crushed ice. Extraction is carried out with chloroform, the organic phase is washed with a decinormal sodium hydroxide solution, it is dried over magnesium sulfate and evaporated under reduced pressure. The residue is stirred for 45 minutes in 40°-60° petroleum spirit, filtered and dried. 5-Phenyl-3-(2-thienylmethylene)-2-furanone (45.3 g), m.p. 141° C., is thereby isolated.

EXAMPLE 4

The reaction is carried out as in Example 2, starting with dimethyl sulfoxide (24 cc), potassium hydroxide powder (3.6 g), N-(1-methylpropyl)-4-phenylbenzo[b]thiophene-6-carboxamide (4 g) and methyl iodide (1.6 cc). After chromatography of the residue over silica gel using a cyclohexane:ethyl acetate (50:50 by volume) mixture as the eluent and recrystallization in isopropyl ether, N-methyl-N-(1-methylpropyl)-4-phenylbenzo[b]thiophene-6-carboxamide (1.2 g), m.p. 84° C., is isolated.

The N-(1-methylpropyl)-4-phenylbenzo[b]thiophene-6-carboxamide may be prepared as follows:

The reaction is carried out as in Example 1, starting with 4-phenylbenzo[b]thiophene-6-carboxylic acid (4 g), thionyl chloride (3.5 cc) and toluene (40 cc) and then 2-butanamine (1.59 cc) and triethylamine (13.3 cc) in toluene (40 cc). This product has a melting point of 194° C.

EXAMPLE 5

The reaction is carried out as in Example 1, but starting with 7-phenylbenzo[b]thiophene-5-carboxylic acid (2.5 g) in toluene (25 cc) and thionyl chloride (2.2 cc) and then triethylamine (4.15 cc) and piperidine (0.97 cc) in toluene (25 cc). After two successive chromatographies of the residue on silica gel, the first with a cyclohexane:ethyl acetate (80:10:10 by volume) mixture as the eluent and the second with a cyclohexane:ethyl acetate (70:30 by volume) mixture as the eluent, a residue is isolated, which is stirred for 1 hour in 40°-60° petroleum spirit. After filtering and drying, 1-[(7-phenylbenzo[b]thien-5-yl)carbonyl]piperidine (1.55 g), m.p. 112° C., is isolated.

EXAMPLE 6

The reaction is carried out as in Example 1, starting with 7-phenylbenzo[b]thiophene-5-carboxylic acid (2.5 g) in toluene (25 cc) and thionyl chloride (2.2 cc) and then triethylamine (4.15 cc) and N-methylaniline (1.06 cc) in toluene (25 cc).

After chromatography of the residue on silica gel using a cyclohexane:ethyl acetate:ethanol (80:10:10 by volume) mixture as the eluent, a residue is isolated, which is stirred for 3 hours in 40°-60° petroleum spirit. After filtering and drying, N-methyl-N-phenyl-7-phenylbenzo[b]thiophene-5-carboxamide (1.9 g), m.p. 127° C., is isolated.

EXAMPLE 7

The reaction is carried out as in Example 1, starting with 7-phenylbenzo[b]thiophene-5-carboxylic acid (3 g) in toluene (30 cc) and thionyl chloride (2.64 cc) and then triethylamine (5 cc) and N-methylethylamine (1.01 cc) in toluene (30 cc). After chromatography of the residue on silica gel using a cyclohexane:ethanol:ethyl acetate (90:5:5 by volume) mixture as the eluent, a residue is obtained, which is stirred overnight in 40°-60° petroleum spirit (50 cc). After filtering and drying, N-ethyl-N-methyl-7-phenylbenzo[b]thiophene-5-carboxamide (1.5 g), m.p. 93° C., is isolated.

EXAMPLE 8

The reaction is carried out as in Example 1, starting with 4-(4-chlorophenyl)benzo[b]thiophene-6-carboxylic acid (4.67 g) in toluene (45 cc) and thionyl chloride (3.6 cc) and then triethylamine (6.9 cc) and diethylamine (1.7 cc) in toluene (45 cc). After chromatography of the residue using a cyclohexane:ethyl acetate (90:10 by volume) mixture as the eluent, a residue is obtained, which is stirred for 2 hours in 40°-60° petroleum spirit. After filtering and drying, N,N-diethyl-4-(4-chlorophenyl)benzo[b]thiophene-6-carboxamide (1.07 g), m.p. 135° C., is obtained.

The 4-(4-chlorophenyl)benzo[b]thiophene-6-carboxylic acid may be prepared as follows:

The reaction is carried out as in Example 1 following the procedure for the preparation of 7-phenylbenzo[b]thiophene-5-carboxylic acid, starting with methanesulfonic acid (5 cc), acetic acid (5 cc) and 5-(4-chlorophenyl)-3-(2-thienylmethylene)-2-furanone (0.0037 mol) and heating at 110° C. instead of 120° C. It has a melting point of 240° C.

The 5-(4-chlorophenyl)-3-(2-thienylmethylene)-2-furanone may be prepared as follows:

The reaction is carried out as in Example 1, following the procedure for the preparation of 5-phenyl-3-(3-thienylmethylene)-2-furanone, starting with 3-(4-chlorobenzoyl)propionic acid (0.05 mol), thiophene-2-carboxaldehyde (0.06 mol), acetic anhydride (14.2 cc) and anhydrous sodium acetate (0.05 mol). It has a melting point of 222° C.

EXAMPLE 9

The reaction is carried out as in Example 1, starting with 4-(4-methoxyphenyl)benzo[b]thiophene-6-carboxylic acid (2.9 g) in toluene (30 cc) and thionyl chloride (2.3 cc) and triethylamine (4.3 cc) and diethylamine (1.1 cc) in anhydrous toluene (30 cc). After chromatography of the residue on silica gel using a cyclohexane:ethyl acetate (80:20 by volume) mixture as the eluent and recrystallization in isopropyl ether, N,N-diethyl-4-(4-methoxyphenyl)benzo[b]thiophene-6-carboxamide (1.12 g), m.p. 88° C., is isolated.

The 4-(4-methoxyphenyl)benzo[b]thiophene-6-carboxylic acid may be prepared as follows:

The reaction is carried out as in Example 1, following the procedure for the preparation of 7-phenylbenzo[b]thiophene-5-carboxylic acid, starting with methanesulphonic acid (10 cc), acetic acid (10 cc) and 5-(4-methoxyphenyl)-3-(2-thienylmethylene)-2-furanone (0.007 mol) and heating at 110° C. instead of 120° C. It has a melting point of 144° C.

The 5-(4-methoxyphenyl)-3-(2-thienylmethylene)-2-furanone may be prepared as follows:

The reaction is carried out as in Example 1, following the procedure for the preparation of 5-phenyl-3-(3-thienylmethylene)-2-furanone, starting with 3-(4-methoxybenzoyl)propionic acid (0.05 mol), thiophene-2-carboxaldehyde (0.06 mol), acetic anhydride (14.2 cc) and anhydrous sodium acetate (0.05 mol). It has a melting point of 175° C.

EXAMPLE 10

7-(3-Nitrophenyl)benzo[b]thiophene-5-carboxylic acid (1.3 g) in thionyl chloride (4 cc) is heated under reflux for 1 hour 30 minutes. The excess thionyl chloride is evaporated under reduced pressure, toluene (30 cc) and triethylamine (1.9 cc) are added to the residue, the mixture is stirred and diethylamine (0.45 cc) is then added dropwise. After stirring at ambient temperature (approximately 20° C.) for 2 hours, the reaction mixture is poured onto ethyl acetate and an aqueous sodium carbonate solution. The organic phase is decanted and the aqueous phase extracted with ethyl acetate. The organic phases are combined, washed with water, dried over magnesium sulfate and evaporated under reduced pressure. The residue obtained is chromatographed under pressure on silica gel using a cyclohexane:ethyl acetate (80:20 by volume) mixture as the eluent. The residue is stirred in 40°-60° petroleum spirit for 2 hours. After filtering and drying, N,N-diethyl-7-(3-nitrophenyl)benzo[b]thiophene-5-carboxamide (1.42 g), m.p. 106° C., is obtained.

The 7-(3-nitrophenyl)benzo[b]thiophene-5-carboxylic acid may be prepared as follows: The reaction is carried out as in Example 1, following the procedure for the preparation of 7-phenylbenzo[b]thiophene-5-carboxylic acid, starting with methane-sulfonic acid (10 cc), acetic acid (10 cc) and 5-(3-nitrophenyl)-3(3-thienylmethylene)-2-furanone (0.0062 mole) and heating at 110° C. instead of 120° C. The product decomposes at approximately 220° C.

The 5-(3-nitrophenyl)-3-(3-thienylmethylene)-2-furanone may be prepared as follows:

The reaction is carried out as in Example 1, following the procedure for the preparation of 5-phenyl-3-(3-thienylmethylene)-2-furanone, starting with 3-(3-nitrobenzoyl)propionic acid (0.023 mol), thiophene-3-carboxaldehyde (0.03 mol), acetic anhydride (6.6 cc) and anhydrous sodium acetate (0.023 mol) and heating at 90° C. instead of 80° C. The product melts below 220° C. with decomposition.

EXAMPLE 11

The reaction is carried out as in Example 10, starting with 7-(3,4-dimethylphenyl)benzo[b]thiophene-5-carboxylic acid (2.5 g) in thionyl chloride (7 cc) and the triethylamine (3.74 cc) and N-methyl-2-butanamine (0.77 g) in anhydrous toluene (30 cc).

After chromatography of the residue under pressure using a cyclohexane:ethyl acetate (85:15 by volume) mixture as the eluent, an oil is isolated, which is crystallized in isopropyl ether. N-Methyl-N-(1-methylpropyl)-7-(3,4-dimethylphenyl)benzo[b]thiophene-5-carboxamide (1.2 g), m.p. 120° C., is thereby isolated.

The 7-(3,4-dimethylphenyl)benzo[b]thiophene-5-carboxylic acid may be prepared as follows:

The reaction is carried out as in Example 1, following the procedure for the preparation of 7-phenylbenzo[b]thiophene-5-carboxylic acid, starting with methanesulfonic acid (20 cc), acetic acid (20 cc) and 5-(3,4-dimethylphenyl)-3-(3-thienylmethylene)-2-furanone (0.014 mol). It decomposes at approximately 250° C.

The 5-(3,4-dimethylphenyl)-3-(3-thienylmethylene)-2-furanone may be prepared as follows:

The reaction is carried out as in Example 1, following the procedure for the preparation of 5-phenyl-3-(3-thienylmethylene)-2-furanone, starting with 3-(3,4-dimethylbenzoyl)propionic acid (0.025 mol), thiophene-3-carboxaldehyde (0.03 mol), acetic anhydride (6.6 cc) and anhydrous sodium acetate (0.025 mol). It decomposes at approximately 250° C.

EXAMPLE 12

The reaction is carried out as in Example 2, starting with N-cyclopropylmethyl-7-phenylbenzo[b]thiophene-5-carboxamide (2 g), methyl iodide (0.8 cc) and potassium hydroxide powder (1.83 g) in dimethyl sulfoxide (12 cc).

After chromatography on silica gel using a cyclohexane:ethyl acetate (80:20 by volume) mixture as the eluent, a residue (1.8 g) is obtained, which is taken up with ethyl ether. The organic phase is washed with water, dried over magnesium sulfate and evaporated under reduced pressure.

N-Cyclopropylmethyl-N-methyl-7-phenylbenzo[b]thiophene-5a-carboxamide (1.1 g), the NMR spectrum in deuterated chloroform of which has the following characteristics, is thereby isolated:

| | |
|---|---|
| H$_4$ | δ: 7.6 ppm |
| H$_6$ | δ: 7.8 ppm |
| other aromatic H | δ: between 7.3 and 8 ppm |
| N—CH$_3$ | δ: 3.1 ppm |
| N—CH$_2$ | δ: 3.3 ppm |
| —CH$_2$—C$\underline{H}$— | δ: 1 ppm |
| C$\underline{H}_2$—C$\underline{H}_2$ (cyclopropyl) | δ: between 0 and 0.8 ppm |

The N-cyclopropylmethyl-7-phenylbenzo[b]thiophene-5-carboxamide may be prepared as follows:

The reaction is carried out as in Example 1, starting with 7-phenylbenzo[b]thiophene-5-carboxylic acid (5.08 g), and thionyl chloride (4.36 cc) in toluene (50 cc) and then cyclopropylmethylamine hydrochloride (2.15 g) and triethylamine (11.3 cc) in toluene (50 cc). Its NMR spectrum is deuterated chloroform has the following characteristics:

| | |
|---|---|
| H$_4$ | δ: 7.8 ppm |
| H$_6$ | δ: 8.2 ppm |
| other aromatic H | δ: between 7.4 and 7.8 ppm |
| NH | δ: 6.5 ppm |
| N—CH$_2$ | δ: 3.3 ppm |

EXAMPLE 13

The reaction is carried out as in Example 2, starting with N-(1-methylpropyl)-7-(2-chlorophenyl)benzo[b]thiophene carboxamide (1.9 g), methyl iodide (0.7 cc) and potassium hydroxide powder (1.55 g) in dimethyl sulfoxide (12 cc).

After chromatography on silica gel using a cyclohexane:ethyl acetate (70:30 by volume) mixture as the eluent, a residue is isolated, which is stirred in 40°-60° petroleum spirit. After filtering and drying, N-methyl-N-(1-methylpropyl)-7-(2-chlorophenyl)-benzo[b]thiophene-5-carboxamide (1.05 g), m.p. 98° C., is obtained.

The N-(1-methylpropyl)-7-(2-chlorophenyl)benzo[b]-thiophene-5-carboxamide may be prepared as follows:

The reaction is carried out as in Example 1, starting with 7-(2-chlorophenyl)benzo[b]thiophene-5-carboxylic acid (2.35 g) and thionyl chloride (1.8 cc) in toluene (23 cc) and then 2-butanamine (0.83 cc) and triethylamine (6.9 cc) in toluene (23 cc). It has a melting point of 125° C.

The 7-(2-chlorophenyl)benzo[b]thiophene-5-carboxylic acid may be prepared as follows:

The reaction is carried out as in Example 1, following the procedure for the preparation of 7-phenylbenzo[b]thiophene-5-carboxylic acid, starting with methanesulfonic acid (22.5 cc), acetic acid (22.5 cc) and 5-(2-chlorophenyl)-3-(3-thienylmethylene)-2-furanone (0.016 mol). It has a melting point of 225° C.

The 5-(2-chlorophenyl)-3-(3-thienylmethylene)-2-furanone may be prepared as follows:

The reaction is carried out as in Example 1, following the procedure for the preparation of 5-phenyl-3-(3-thienylmethylene)-2-furanone, starting with 3-(2-chlorobenzoyl)propionic acid (0.017 mol), thiophene-3-carboxaldehyde (0.021 mol), acetic anhydride (4.9 cc) and anhydrous sodium acetate (0.17 mol).

EXAMPLE 14

The reaction is carried out as in Example 2, starting with N-(1-methylpropyl)-7-(2-fluorophenyl)benzo[b]-thiophene-5-carboxamide (2.65 g), methyl iodide (1 cc) and potassium hydroxide powder (2.3 g) in dimethyl sulfoxide (16 cc).

After chromatography on silica gel using a cyclohexane:ethyl acetate (70:30 by volume) mixture as the eluent, a residue is isolated, which is stirrred in 40°–60° petroleum spirit for 30 minutes. After filtering and drying, N-methyl-N-(1-methylpropyl)-7-(2-fluorophenyl)-benzo[b]thiophene-5-carboxamide (0.85 g), m.p. 89° C., is obtained.

The N-(1-methylpropyl)-7-(2-fluorophenyl)benzo[b]-thiophene-5-carboxamide may be prepared as follows:

The reaction is carried out as in Example 1, starting with 7-(2-fluorophenyl)benzo[b]thiophene-5-carboxylic acid (3.2 g) and thionyl chloride (2.6 cc) in toluene (32 cc) and then 2-butanamine (1.2 cc) and triethylamine (9.9 cc) in toluene (32 cc). It has a melting point of 185° C.

The 7-(2-fluorophenyl)benzo[b]thiophene-5-carboxylic acid may be prepared as follows:

The reaction is carried out as in Example 1, following the procedure for the preparation of 7-phenylbenzo[b]-thiophene-5-carboxylic acid, starting with methanesulfonic acid (44 cc), acetic acid (44 cc) and 5-(2-fluorophenyl)-3-(3-thienylmethylene)-2-furanone (0.032 mol). It has a melting point of 223° C.

The 5-(2-fluorophenyl)-3-(3-thienylmethylene)-2-furanone may be prepared as follows:

The reaction is carried out as in Example 1, following the procedure for the preparation of 5-phenyl-3-(3-thienylmethylene)-2-furanone, starting with 3-(2-fluorobenzoyl)propionic acid (0.037 mol), thiophene-3-carboxaldehyde (0.045 mol), acetic anhydride (10.5 cc) and anhydrous sodium acetate (0.037 mol). It has a melting point of 88° C.

EXAMPLE 15

The reaction is carried out as in Example 1, starting with 7-(3-trifluoromethylphenyl)benzo[b]thiophene-5-carboxylic acid (2 g) in toluene (20 cc) and thionyl chloride (1.4 cc) and then N-methyl-2-butanamine hydrochloride (0.77 g) and triethylamine (6.1 cc) in toluene (20 cc).

After two successive chromatographies on silica gel, the first using a cyclohexane:ethyl acetate (70:30 by volume) mixture as the eluent and the second using a cyclohexane:ethyl ether (70:30 by volume) mixture as the eluent, N-methyl-N-(1-methylpropyl)-7-(3-trifluoromethylphenyl)benzo[b]thiophene-5-carboxamide (1.1 g) is obtained in the form of a yellow oil, the NMR spectrum of which in deuterated chloroformhas the following characteristics:

| H4 | δ: 7.6 ppm |
| H6 | δ: 7.9 ppm |
| other aromatic H | δ: between 7.3 and 8 ppm |
| N—CH3 | δ: 2.9 ppm |
| N—CH—CH3 | δ: 1.2 ppm |
| N—CH—CH2—CH3 | δ: 1.6 ppm |
| N—CH—CH2—CH3 | δ: 0.8 ppm |

The 7-(3-trifluoromethylphenyl)benzo[b]thiophene-5-carboxylic acid may be prepared as follows:

The reaction is carried out as in Example 1, following the procedure for the preparation of 7-phenylbenzo[b]-thiophene-5-carboxylic acid, starting wwith methanesulfonic acid (15 cc), acetic acid (15 cc) and 5-(3-trifluoromethylphenyl)-3-(3-thienylmethylene)-2-furanone (0.0092 mol). It has a melting point of 150° C.

The 5-(3-trifluoromethylphenyl)-3-(3-thienylmethylene)-2-furanone may be prepared as follows:

The reaction is carried out as in Example 1, following the procedure for the preparation of 5-phenyl-3-(3-thienylmethylene)-2-furanone, starting with 3-(3-trifluoromethylbenzoyl)propionic acid (0.012 mol), thiophene-3-carboxaldehyde (0.0146 mol), acetic anhydride (3.45 cc) and anhydrous sodium acetate (0.012 mol). It has a melting point of 192° C.

EXAMPLE 16

The reaction is carried out as in Example 1, starting with 4-phenylbenzo[b]furan-6-carboxylic acid (1 g) in toluene (10 cc) and thionyl chloride (0.92 cc) and then triethylamine (3.5 cc) and diethylamine (0.43 cc) in toluene (10 cc).

After two successive chromatographies on silica gel, the first using a cyclohexane:ethanol:ethyl acetate (80:10:10 by volume) mixture as the eluent and the second using a cyclohexane:ethanol:ethyl acetate (92:4:4 by volume) mixture as the eluent, a residue (0.6 g) is obtained, which is chromatographed under pressure on silica gel using a cyclohexane:ethyl acetate (85:15 by volume) mixture as the eluent. N,N-Diethyl-4-phenyl-benzo[b]furna-6-carboxamide (0.32 g) is obtained in the form of a thick oil, the proton NMR of which in dueterated chloroform has the following characteristics:

| H2 | δ: 7.8 ppm |
| H3 | δ: 6.9 ppm |
| other aromatic H | δ: between 7.4 and 7.7 ppm |
| CH3 | δ: 1.2 ppm |
| CH2 | δ: 3.4 ppm |

The 4-phenylbenzo[b]furan-6-carboxylic acid may be prepared as follows:

The reaction is carried out as in Example 1, following the procedure for the preparation of 7-phenylbenzo[b]-thiophene-5-carboxylic acid, starting with methanesulfonic acid (600 cc), acetic acid (600 cc) and 3-(2-furylmethylene)-5-phenyl-2-furanone (0.521 mol). It has a melting point of 180° C.

The 3-(2-furylmethylene)-5-phenyl-2-furanone may be prepared as follows:

The reaction is carried out as in Example 1, following the procedure for the preparation of 5-phenyl-3-(3-thienylmethylene)-2-furanone, starting with 3- benzoyl-propionic acid (0.5 mol), furan-2-carboxaldehyde (0.6 mol), acetic anhydride (142 cc) and anhydrous sodium acetate (0.5 mol). It has a melting point of 117° C.

EXAMPLE 17

The reaction is carried out as in Example 1, starting with 4-phenylbenzo[b]furan-6-carboxylic acid (1.1 g) in toluene (11 cc) and thionyl chloride (1.01 cc) and then triethylamine (4.6 cc) and N-methyl-2-butanamine (0.57 g) in toluene (11 cc).

After two successive chromatographies on silica gel, the first using a cyclohexane:ethyl acetate:ethanol (80:10:10 by volume) mixture as the eluent, and the second using a cyclohexane:ethanol:ethyl acetate (92:4:4 by volume) mixture as the eluent, a residue (0.6 g) is obtained, which is chromatographed under pressure on silica gel using a cyclohexane:ethyl acetate (85:15 by volume) as the eluent.

N-Methyl-N-(1-methylpropyl)-4-phenylbenzo[b]furan-6-carboxamide (0.35 g) is obtained in the form of an oil, the proton NMR of which in deuterated chloroform has the following characteristics:

| H$_2$ | δ: 7.8 ppm |
| H$_3$ | δ: 6.9 ppm |
| other aromatic H | δ: between 7.4 and 7.7 ppm |
| N—CH$_3$ | δ: 2.9 ppm |
| CH—C<u>H</u>$_3$ | δ: 1.2 ppm |
| C<u>H</u>—CH$_3$ | δ: 4.8 and 3.8 ppm |
| <u>CH</u>$_2$—CH$_3$ | δ: 1.5 ppm |
| CH$_2$—C<u>H</u>$_3$ | δ: 0.8 ppm |

EXAMPLE 18

The reaction is carried out as in Example 1, starting with 7-phenylbenzo[b]furan-5-carboxylic acid (4 g) in toluene (20 cc) and thionyl chloride (7.4 cc) and then diethylamine (1.7 cc) and triethylamine (14.1 cc)in toluene (40 cc).

After two successive chromatographies on silica gel, the first using a cyclohexane:ethanol:ethyl acetate (90:5:5 by volume) mixture as the eluent, the second using a cyclohexane:ethylacetate (80:20 by volume) mixture as the eluent, a residue is isolated, which is stirred in 40°-60° petroleum spirit for one hour.

After filtering and drying, N,N-diethyl-7-phenylbenzo[b]furan-5-carboxamide (2.75 g), m.p. 56° C., is obtained.

The 7-phenylbenzo[b]furan-5-carboxylic acid may be prepared as follows:

The reaction is carried out as in Example 1, following the procedure for the preparation of 7-phenylbenzo[b]thiophene-5-carboxylic acid, starting with methanesulfonic acid (31 cc), acetic acid (31 cc)and 3-(3-furylmethylene)-5-phenyl-2-furanone (0.0263 mol). It has a melting point of 197° C.

The 3-(3-furylmethylene)-5-phenyl-2-furanone may be prepared as follows:

The reaction is carried out as in Example 1, following the procedure for the preparation of 5-phenyl-3-(3-thienylmethylene)-2-furanone, starting with 3-benzoylpropionic acid (0.23 mol), furan-3-carboxaldehyde (0.276 mol), acetic anhydride (65.2 cc) and anhydrous sodium acetate (0.23 mol). It has a melting point of 174° C.

EXAMPLE 19

The reaction is carried out as in Example 2, starting with N-(1-methylpropyl)-7-phenylbenzo[b]furan-5-carboxamide (3 g), methyl iodide (1.9 cc) and potassium hydroxide powder (2.9 g) in dimethyl sulfoxide (18 cc).

After two successive chromatographies on silica gel, the first using a cyclohexane:ethyl acetate (70:30 by volume) mixture as the eluent and the second using ethyl ether as the eluent, N-methyl-N-(1-methylpropyl)-7-phenylbenzo[b]furan-5-carboxamide (2.55 g) is obtained, the proton NMR of which in deuterated chloroform has the following characteristics:

| H$_2$ | δ: 7.8 ppm |
| H$_3$ | δ: 6.9 ppm |
| other aromatic H | δ: between 7.3 and 8 ppm |
| N—CH$_3$ | δ: 2.9 ppm |
| CH—C<u>H</u>$_3$ | δ: 1.2 ppm |
| C<u>H</u>—CH$_3$ | δ: 4.8 and 3.8 ppm |
| <u>CH</u>$_2$—CH$_3$ | δ: 1.5 ppm |
| CH$_2$—C<u>H</u>$_3$ | δ: 0.9 ppm |

The N-(1-methylpropyl)-7-phenylbenzo[b]furan-5-carboxamide may be prepared as follows:

The reaction is carried out as in Example 1, starting with 7-phenylbenzo[b]furan-5-carboxylic acid (8 g) and thionyl chloride (14.8 cc) in toluene (40 cc) and then 2-butanamine (3.4 cc) and triethylamine (17.2 cc) in toluene (80 cc).

EXAMPLE 20

The reaction is carried out as in Example 1, starting with 7-(2-thienyl)benzo[b]furan-5-carboxylic acid (3.5 g) in toluene (17.5 cc) and thionyl chloride (3.15 cc) and then triethylamine (12 cc) and diethylamine (1.47 cc) in toluene (35 cc).

After chromatography on silica gel using a cyclohexane:ethyl acetate (70:30 by volume) mixture as the eluent, an oil is obtained which crystallizes in petroleum spirit. N,N-Diethyl-7-(2-thienyl)benzo[b]furan-5-carboxamide (1.8 g), m.p. 64° C., is thereby isolated.

The 7-(2-thienyl)benzo[b]furan-5-carboxylic acid may be prepared as follows:

The reaction is carried out as in Example 1, following the procedure for the preparation of 7-phenylbenzo[b]thiophene-5-carboxylic acid, starting with methanesulfonic acid (90 cc), acetic acid (90 cc) and 3-(3-furylmethylene)-5(2-thienyl)-2-furanone (0.071 mol). It has a melting point of 192° C.

The 3-(3-furylmethylene)-5-(2-thienyl)-2-furanone may be prepared as follows:

The reaction is carriedout as in Example 1, following the procedure for the preparation of 5-phenyl-3-(3-thienylmethylene)-2-furanone, starting with 4-oxo-4-(2-thienyl)butyric acid (0.102 mol), furan-3-carboxaldehyde (0.122 mol), acetic anhydride (29 cc) and anhydrous sodium acetate (0.102 mol). It has a melting point of 114° C.

EXAMPLE 21

The reaction is carried out as in Example 1, starting with 7-(2-thienyl)benzo[b]furan-5-carboxylic acid (4 g) in toluene (20 cc) and thionyl chloride (3.6 cc) and then triethylamine (16.1 cc) and N-methyl-2-butanamine hydrochloride (2.2 g) in toluene (40 cc).

After chromatography on silica gel using a cyclohexane:ethyl acetate (70:30 by volume) mixture as the eluent, N-methyl-N-(1-methylpropyl)-7-(2-thienyl)benzo[b]furan-5-carboxamide (1.5 g), m.p. 96° C., is isolated.

The invention includes within its scope pharmaceutical compositions comprising a compoundof formula (I), which may, when the group NR$_1$R$_2$ contains at least one asymmetric carbon atom, be in the form of a racemate or a stereoisomer, in combination with one or more compatible pharmaceutically acceptable adjuvants or diluents which may be inert or physiologically active. These compositions may be administered by the oral, parenteral or rectal route or locally.

Tablets, pills, powders (gelatin capsules or cachets) or granules, may be used as solid compositions for oral administration. In these compositions, the active ingredient according the the invention may be mixed with one or more inert diluents such as starch, cellulose, sucrose, lactose or silica. These compositions may also contain substances other than diluents, for example one or more lubricants such as magnesium stearate or talcum, a colorant, a coating (dragees) or a lacquer.

Pharmaceutically acceptable solutions, suspensions, emulsions, syrups and elixirs containing inert diluents such as water, ethanol, glycerol, vegetable oils or liquid paraffin may be used as liquid compositions for oral administration. These compositions may contain substances other than diluents, for example wetting agents, sweeteners, thickeners, flavoring agents or stabilizers.

Sterile compositions for parenteral administration may preferably be non-aqueous solutions, suspensions or emulsions. Water, propylene glycol, polyethylene glycol, vegetable oils, especially olive oil, injectable organic acid esters, for example ethyl oleate or other suitable organic solventsmay be used as the solvent or the carrier.

These compositions may also contain adjuvants, especially wetting agents, tonicity regulating agents, emulsifiers, dispersants and stabilizers. The sterilization may be carried out in several ways, for example by aseptic filtration, incorporating a sterilizing agent, by irradiation or by heating. They may also be prepared in the form of sterile solid compositions which may be dissolved at the time of use in a sterile medium suitable for injection.

Compositions for rectal administration are suppositories or rectal capsules, which contain, in addition to the active product, excipients such as cocoa butter, semi-synthetic glycerides or polyethylene glycols.

Compositions for local administration may be for example creams, ointments, lotions, eye lotions, mouthwashes, nasal drops or aerosols.

In human therapeutics, the compounds according to the invention are particularly useful as anxiolytic, antianginal and immunomodulatory agents.

The dosage depends on the effect sought, the length of treatment and the administration route employed; it is generally 10 to 500 mg per day by the oral route for an adult, with unit doseas ranging from 2 to 100 mg of the active ingredient. In general, the medical practitioner will determine the appropriate dosage depending on the age, weight and all other factors specific to the subject to be treated.

The following Examples illustrate compositions according to the invention:

EXAMPLE A

Capsules containing 50 mg of active product with the following composition are prepared according to the conventional technique:

| | |
|---|---|
| N—Methyl-N—(1-methylpropyl)-4-phenylbenzo[b]-thiophene-6-carboxamide | 50 mg |
| Cellulose | 18 mg |
| Lactose | 55 mg |
| Colloidal silica | 1 mg |
| Carboxymethyl starch sodium salt | 10 mg |
| Talcum | 10 mg |
| Magnesium stearate | 1 mg |

EXAMPLE B

Tablets containing 50 mg of active product with the following composition are prepared according to the conventional technique:

| | |
|---|---|
| N—methyl-N—(1-methylpropyl)-7-(2-chloro-phenyl)benzo[b]thiophene-5-carboxamide | 50 mg |
| Lactose | 104 mg |
| Cellulose | 40 mg |
| Polyvidone | 10 mg |
| Carboxymethyl starch sodium salt | 22 mg |
| Talcum | 10 mg |
| Magnesium stearate | 2 mg |
| Colloidal silica | 2 mg |
| Mixture of hydroxymethylcellulose, glycerine and titanium oxide (72:3.5:24.5) q.s. | 1 tablet |
| film-coated and finished to | 245 mg |

EXAMPLE C

An injectable solution containing 10 mg of active product with the following composition is prepared:

| | |
|---|---|
| N—Methyl-N—(1-methylpropyl)-4-phenyl benzo[b]furan-6-carboxamide | 10 mg |
| Benzoic acid | 80 mg |
| Benzyl alcohol | 0.06 cc |
| Sodium benzoate | 80 mg |
| 95% ethanol | 0.4 cc |
| Sodium hydroxide | 24 mg |
| Propylene glycol | 1.6 cc |
| Water q.s. | 4 cc |

We claim:

1. A compound of formula:

$$\text{X} \underset{\text{Ar}}{\underbrace{\phantom{XXXX}}} \text{—CO—N} \genfrac{}{}{0pt}{}{R_1}{R_2} \quad (I)$$

in which $R_1$ and $R_2$, which may be identical or different, each represent a straight- or branched-chain alkyl group of 1 to 4 carbon atoms, a cycloalkylalkyl group having 1 to 3 carbon atoms in the alkyl and 3 to 6 carbon atoms in the cycloalkyl, or a phenyl group, and $R_1$ and $R_2$, together with the nitrogen atom to which they are attached, may also form a piperidine ring, Ar represents phenyl, thienyl, or phenyl substitutedby one or two substituents selected from the group consisting of halogen, alkyl of 1 to 4 carbon atoms, alkoxy of 1 to 4 carbon atoms, nitro, and trifluoromethyl groups, and X< represents one of the following linkages:

$$\underset{}{\overset{S}{\diagdown}}\,,\quad \underset{S}{\overset{}{\diagdown}}\,,\quad \underset{}{\overset{O}{\diagdown}}\,,\quad \text{and}\quad \underset{O}{\overset{}{\diagdown}}$$

including, when the group NR$_1$R$_2$ contains at least one asymmetric carbon atom, its racemic forms and stereoisomers.

2. A compound as claimed in claim 1, in which R$_1$ and R$_2$, which may be identical or different, are each straight- or branched-chain alkyl of 1 to 4 carbon atoms and Ar is phenyl, phenyl substituted by halogen or nitro, or 2-thienyl including, when the group NR$_1$R$_2$ contains at least one asymmetric carbon atom, its racemic forms and stereoisomers.

3. A compound according to claim 1 which is N-methyl-N-(1-methylpropyl)-4-phenylbenzo[b]furan-6-carboxamide, including its racemic forms and stereoisomers.

4. A compound according to claim 1 which is N-methyl-N-(1-methylpropyl)-7-(2-chlorophenyl)benzo[b]thiophene-5-carboxamide, including its racemic forms and stereoisomers.

5. A compound according to claim 1 which is N-methyl-N-(1-methylpropyl)-4-phenylbenzo[b]thiophene-6-carboxamide, including its racemic forms and stereoisomers.

6. A compound according to claim 1 which is N-methyl-N-(1-methylpropyl)-7-(2-fluorophenyl)benzo[b]thiophene-5-carboxamide, including its racemic forms and stereoisomers.

7. A compound according to claim 1 which is N,N-diethyl-7-(3-nitrophenyl)benzo[b]thiophene-5-carboxamide.

8. A compound according to claim 1 which is N-methyl-N-(1-methylpropyl)-7-(2-thienyl)benzo[b]furan-5-carboxamide, including its racemic forms and stereoisomers.

9. A compond according to claim 1 which is N-methyl-N-(1-methylpropyl)-7-phenylbenzo[b]thiophene-5-carboxamide, including its racemic forms and stereoisomers.

10. A pharmaceutical composition useful as an anxiolytic, antianginal or immunomodulatory agent comprising 2 to 100 mg of a compound as claimed in claim 1 in combination with one or more compatible and pharmaceutically acceptable adjuvants or diluents.

11. Method of treating a human adult in need of anxiolytic, antianginal or immunomodulatory therapy which comprises administering to such human adult 10 to 500 mg per day by the oral route of a compound as claimed in claim 1.

* * * * *